(12) United States Patent
Bales

(10) Patent No.: US 12,268,421 B2
(45) Date of Patent: Apr. 8, 2025

(54) SURGICAL SYSTEM AND METHODS OF USE

(71) Applicant: WARSAW ORTHOPEDIC INC., Warsaw, IN (US)

(72) Inventor: Joel Bales, Hernando, MS (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 0 days.

(21) Appl. No.: 18/089,756

(22) Filed: Dec. 28, 2022

(65) Prior Publication Data

US 2024/0216021 A1 Jul. 4, 2024

(51) Int. Cl.
  *A61B 17/70* (2006.01)

(52) U.S. Cl.
  CPC ...... *A61B 17/7047* (2013.01); *A61B 17/7034* (2013.01)

(58) Field of Classification Search
  CPC .............. A61B 17/7049; A61B 17/705; A61B 17/7062–7068; A61B 17/7034–7037; A61B 17/7032; A61B 17/7001; A61B 17/7047; A61B 17/7056; A61B 17/707
  See application file for complete search history.

(56) References Cited

U.S. PATENT DOCUMENTS

| | | | | |
|---|---|---|---|---|
| 10,321,939 | B2* | 6/2019 | Lee | A61B 17/7049 |
| 10,952,856 | B2* | 3/2021 | Freese | A61F 2/2846 |
| 11,259,846 | B1* | 3/2022 | Yu | A61B 17/7052 |
| 11,596,446 | B2* | 3/2023 | Zhang | A61B 17/7008 |
| 2008/0243186 | A1* | 10/2008 | Abdou | A61B 17/7032 606/246 |
| 2009/0259256 | A1* | 10/2009 | Miller | A61B 17/705 606/250 |

(Continued)

FOREIGN PATENT DOCUMENTS

| | | |
|---|---|---|
| EP | 3366242 A1 | 12/2021 |
| EP | 3995093 A1 | 7/2023 |

(Continued)

OTHER PUBLICATIONS

International Search Report. Appl No. PCT/IB2023/062894. 4 pgs. Apr. 18, 2024.

*Primary Examiner* — Ellen C Hammond
*Assistant Examiner* — Holly Joanna Lane
(74) *Attorney, Agent, or Firm* — Sorell, Lenna & Schmidt, LLP

(57) ABSTRACT

A spinal implant includes a first wall. A first portion includes spaced apart first and second assemblies each extending from a first side of the first wall. The first assembly includes spaced apart first and second extensions. The second assembly includes spaced apart third and fourth extension. The first and second extensions define a first opening. The third and fourth extensions define a second opening. A space between the first assembly and the second assembly defines a cavity configured for disposal of a bone fastener. The head and the openings are configured for disposal of a first spinal rod. A second portion extends from an opposite second side of the first wall. The second portion includes a second wall that is spaced apart from the first wall. Opposing surfaces of the walls define a channel configured for disposal of a second spinal rod.

20 Claims, 9 Drawing Sheets

(56) References Cited

U.S. PATENT DOCUMENTS

| | | | |
|---|---|---|---|
| 2010/0249843 A1* | 9/2010 | Wegrzyn, III | A61B 17/705 |
| | | | 606/264 |
| 2010/0256683 A1* | 10/2010 | Iott | A61B 17/7002 |
| | | | 606/278 |
| 2014/0277160 A1* | 9/2014 | Ziolo | A61B 17/7049 |
| | | | 606/278 |
| 2018/0070994 A1* | 3/2018 | Leff | A61B 17/7079 |
| 2020/0000495 A1 | 1/2020 | Italiaie et al. | |

FOREIGN PATENT DOCUMENTS

| | | | |
|---|---|---|---|
| KR | 20080112851 A * | 12/2008 | A61B 17/705 |
| WO | 20220132852 A1 | 6/2022 | |

* cited by examiner

SURGICAL SYSTEM AND METHODS OF USE

TECHNICAL FIELD

The present disclosure generally relates to medical devices for the treatment of musculoskeletal disorders, and more particularly to a surgical system and method for correction of a spine disorder.

BACKGROUND

Spinal pathologies and disorders such as scoliosis and other curvature abnormalities, kyphosis, degenerative disc disease, disc herniation, osteoporosis, spondylolisthesis, stenosis, tumor, and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes correction, fusion, fixation, discectomy, laminectomy and implantable prosthetics. Correction treatments used for positioning and alignment may employ implants, such as vertebral rods and bone screws for stabilization of a treated section of a spine. This disclosure describes an improvement over these prior technologies.

SUMMARY

In one embodiment, in accordance with the principles of the present disclosure, a spinal implant comprises a body including a first wall. A first portion comprises spaced apart first and second assemblies each extending from a first side of the first wall. The first assembly comprises spaced apart first and second extensions. The second assembly comprises spaced apart third and fourth extensions. The first and second extensions define a first opening. The third and fourth extensions define a second opening. A space between the first assembly and the second assembly define a cavity configured for disposal of a head of a bone fastener. The head and the openings are configured for disposal of a first spinal rod therein. A second portion extends from an opposite second side of the first wall. The second portion comprises a second wall that is spaced apart from the first wall. Opposing surfaces of the walls defining a channel configured for disposal of a second spinal rod.

In one embodiment, in accordance with the principles of the present disclosure, a surgical system comprises a spinal implant including a body having a first wall. The spinal implant includes a first portion comprising spaced apart first and second assemblies each extending from a first side of the first wall. The first assembly comprises spaced apart first and second extensions. The second assembly comprises spaced apart third and fourth extensions. The first and second extensions define a first opening. The third and fourth extensions define a second opening. A space between the first assembly and the second assembly define a cavity. The spinal implant includes a second portion extending from an opposite second side of the first wall. The second portion comprises a second wall that is spaced apart from the first wall. Opposing surfaces of the walls define a channel. A bone fastener has a head positioned in the cavity. A first spinal rod is disposed in the head and the openings. A second spinal rod is disposed in the channel.

In one embodiment, in accordance with the principles of the present disclosure, a surgical system comprises a monolithic spinal implant including a body having a first wall. The spinal implant includes a first portion comprising spaced apart first and second assemblies each extending from a first side of the first wall. The first assembly comprises spaced apart first and second extensions. The second assembly comprises spaced apart third and fourth extensions. The first and second extensions define a first opening. The third and fourth extensions define a second opening. A space between the first assembly and the second assembly define a cavity. The spinal implant includes a second portion extending from an opposite second side of the first wall. The second portion comprises a second wall that is spaced apart from the first wall. Opposing surfaces of the walls define a channel. A bone fastener has a head positioned in the cavity. A first spinal rod is disposed in the head and the openings. A second spinal rod is disposed in the channel. The first extension includes a first surface defining a first threaded hole extending therethrough and a second surface extending from the first surface. The second surface extends at an acute angle relative to the first surface. The third extension includes a third surface defining a second threaded hole extending therethrough and a fourth surface extending from the third surface, the fourth surface extending at an acute angle relative to the third surface. The surgical system comprises a first set screw disposed in the first threaded hole and a second set screw disposed in the second threaded hole such that the set screws directly engage the first spinal rod. The second side includes spaced apart first and second threads. The second wall includes spaced apart third and fourth threads. The surgical system comprises a third set screw disposed with the first and third threads and a fourth set screw disposed with the second and fourth threads such that the third and fourth set screws directly engage the second spinal rod.

Additional features and advantages of various embodiments will be set forth in part in the description that follows, and in part will be apparent from the description, or may be learned by practice of various embodiments. The objectives and other advantages of various embodiments will be realized and attained by means of the elements and combinations particularly pointed out in the description and appended claims.

BRIEF DESCRIPTION OF THE DRAWINGS

The present disclosure will become more readily apparent from the specific description accompanied by the following drawings, in which.

DETAILED DESCRIPTION

Figure 1:
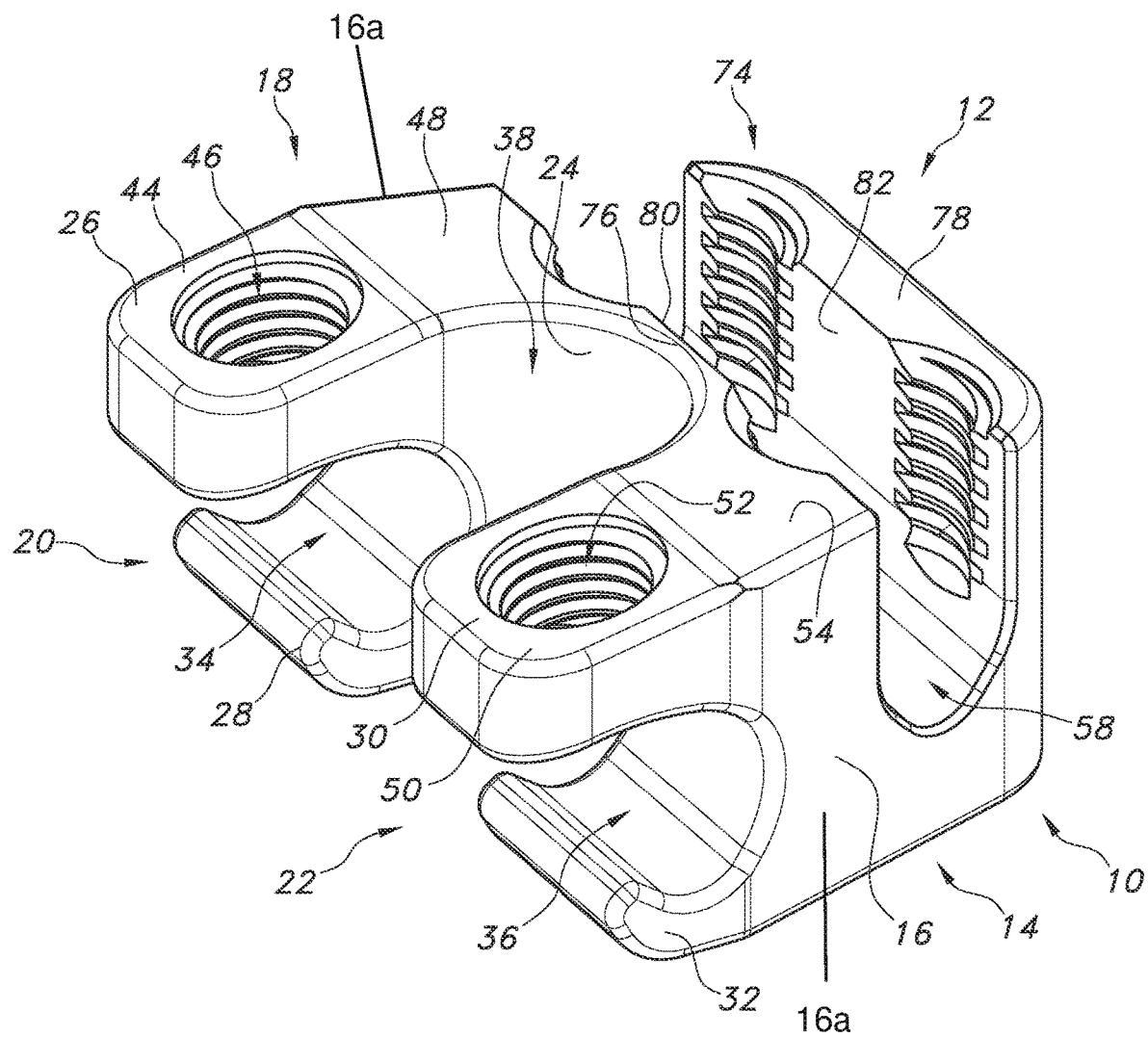
FIG. 1 is a perspective view of a spinal implant of a surgical system, in accordance with the principles of the present disclosure.

For the purposes of this specification and appended claims, unless otherwise indicated, all numbers expressing quantities of amounts, percentages or proportions of materials, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding the numerical ranges and parameters set forth herein, the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "1 to 10" includes any and all subranges between (and including) the minimum value of 1 and the maximum value of 10, that is, any and all subranges having a minimum value of equal to or greater than 1 and a maximum value of equal to or less than 10, e.g., 5.5 to 10.

This disclosure is directed to a surgical system that includes a spinal implant, such as for example, a domino with greater than 2 holes for attaching a roughly parallel rod where the domino is able to be placed around an existing screw head. In particular, a four hole domino is disclosed herein that has greater robustness than a two hole domino. It will be appreciated by on of ordinary skill in the art, that with the disclosed four hole domino, there is a greater need for run on rod than if a smaller counterpart, such as, for example, a two hole domino were used. The opportunity presented by the disclosed four hole domino for two spaced of run on rod greater than 10 mm on each side of a screw head is more likely than a single space of 20 mm of run on rod. As such, a domino such as that disclosed herein that can be mounted on both sides of an existing screw head has an advantage over a long run on rod required domino (e.g., a two hole domino).

Reference will now be made in detail to certain embodiments of the invention, examples of which are illustrated in the accompanying drawings. While the invention will be described in conjunction with the illustrated embodiments, it will be understood that they are not intended to limit the invention to those embodiments. On the contrary, the invention is intended to cover all alternatives, modifications, and equivalents that may be included within the invention as defined by the appended claims.

Figure 2:
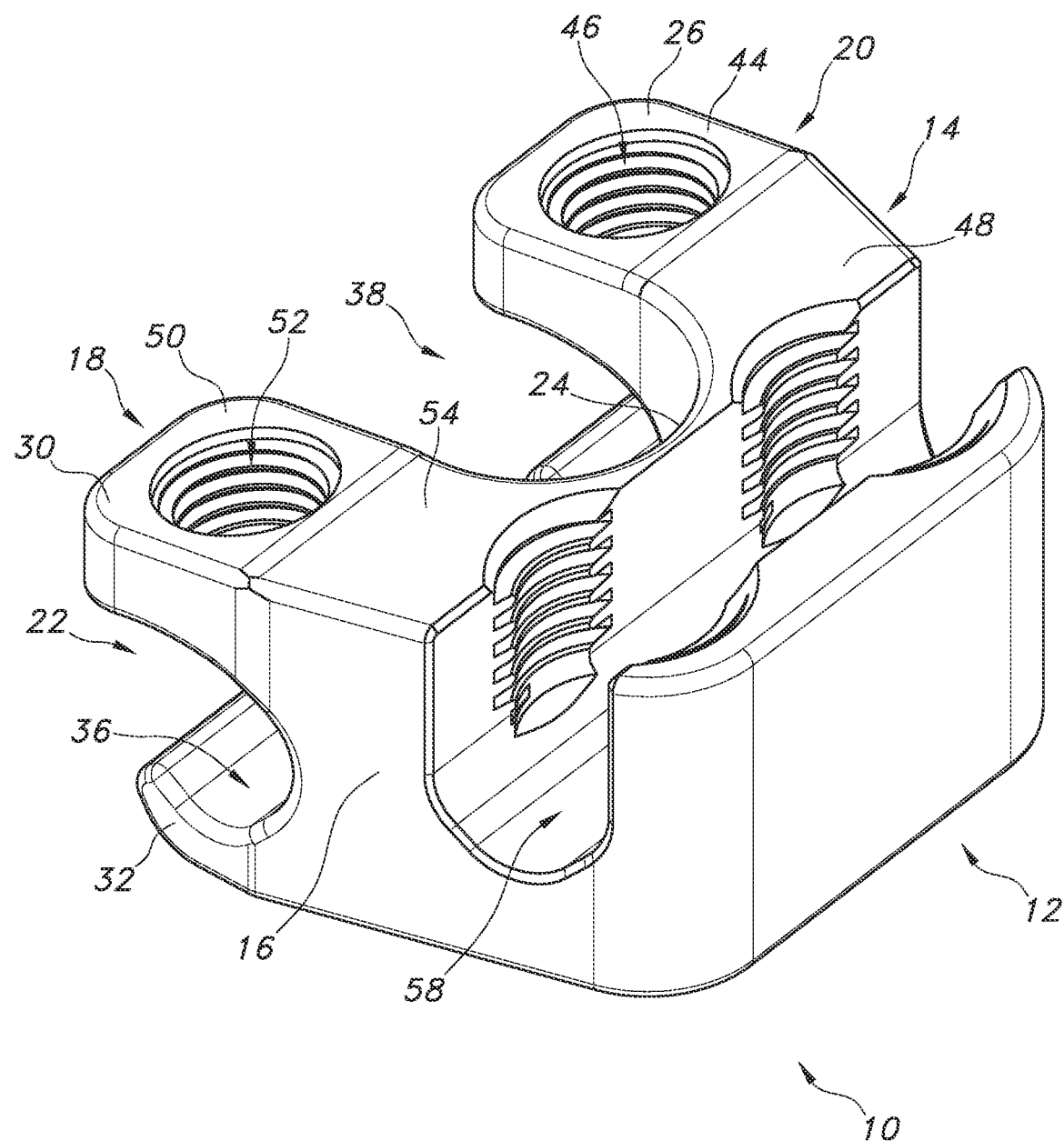
FIG. 2 is a perspective view of the spinal implant shown in FIG. 1.
Figure 3:
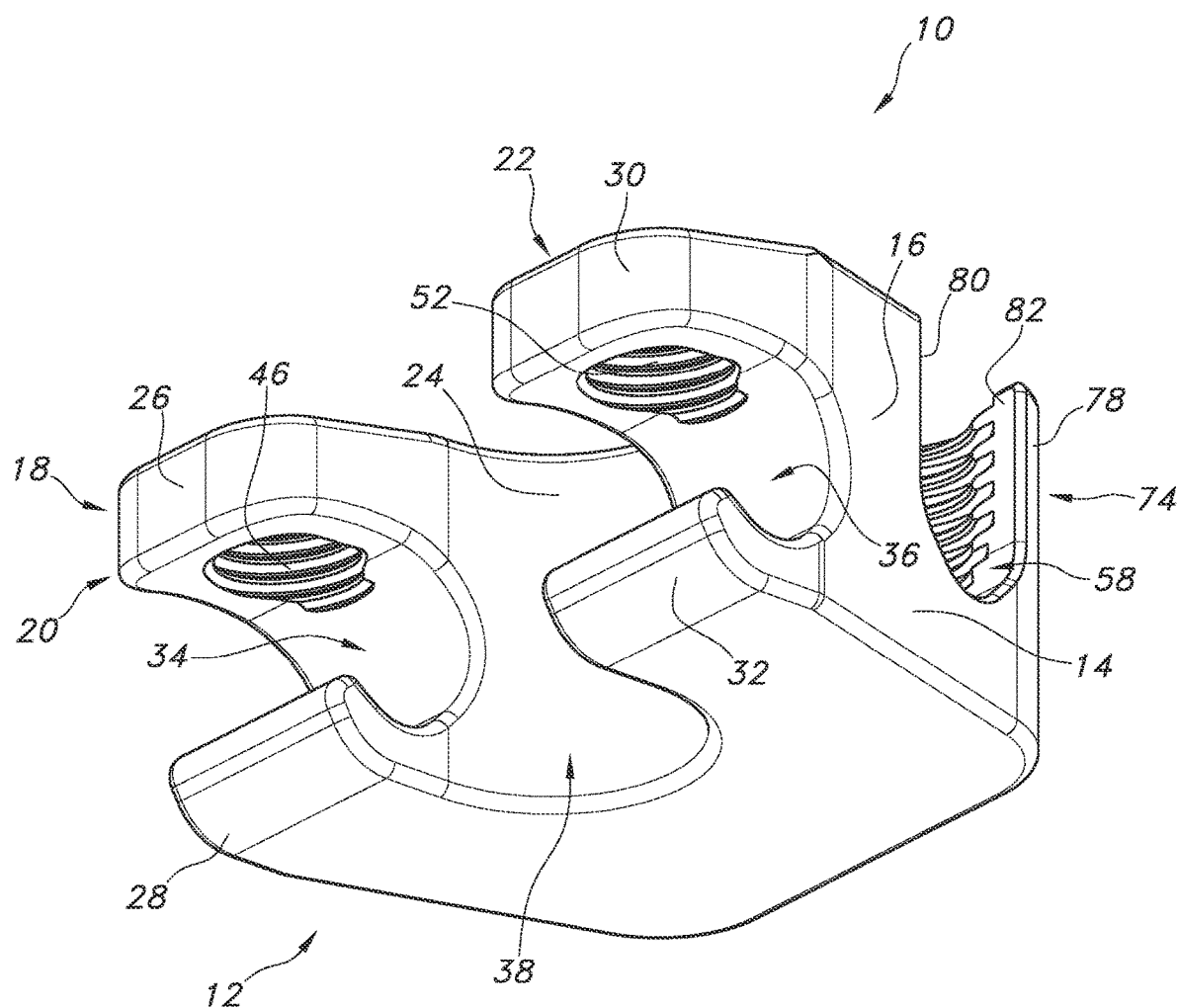
FIG. 3 is a perspective view of the spinal implant shown in FIG. 1.
Figure 5:
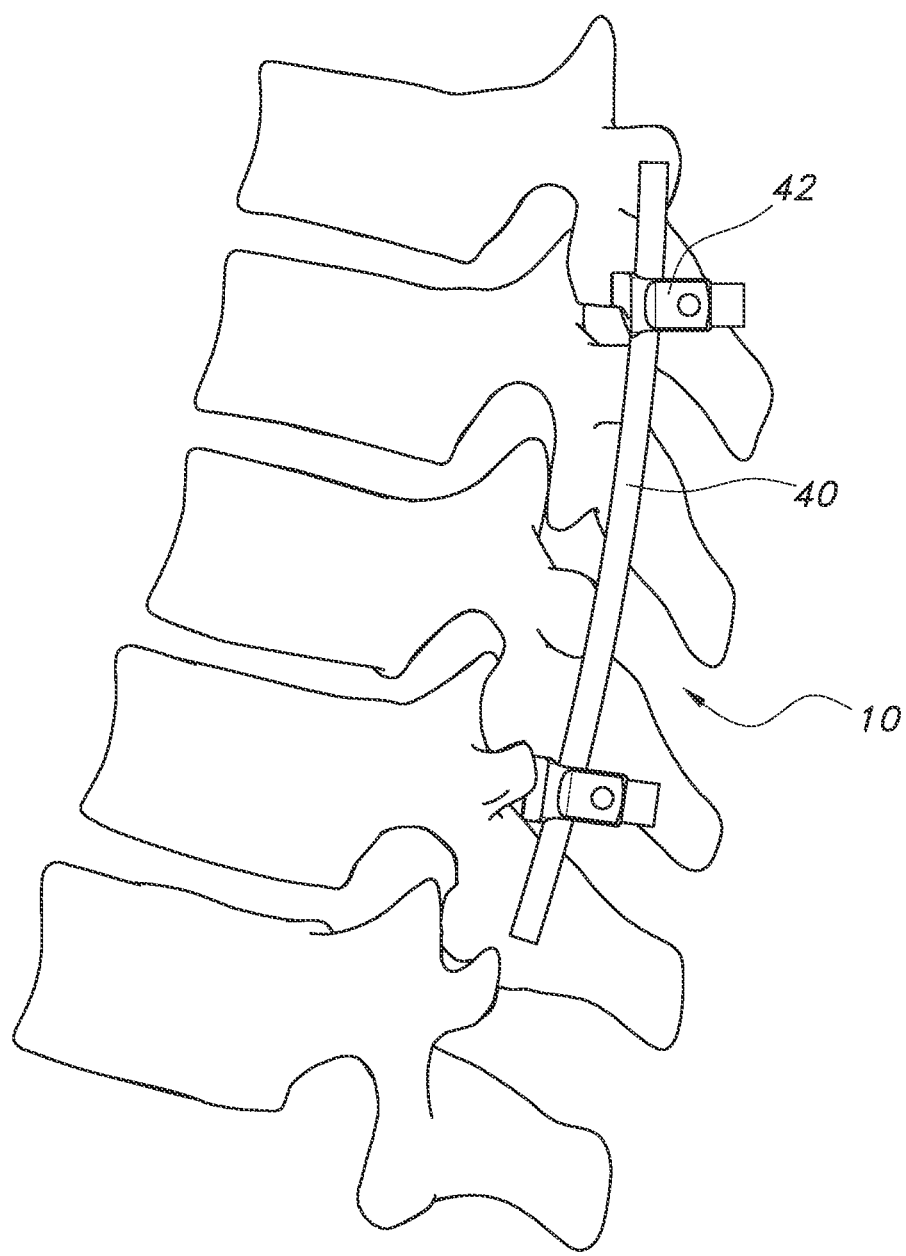
FIG. 5 is a plan view showing the bone fastener shown in FIG. 4 disposed with vertebra and a spinal rod of the surgical system disposed with the bone fastener, in accordance with the principles of the present disclosure.
Figure 6:
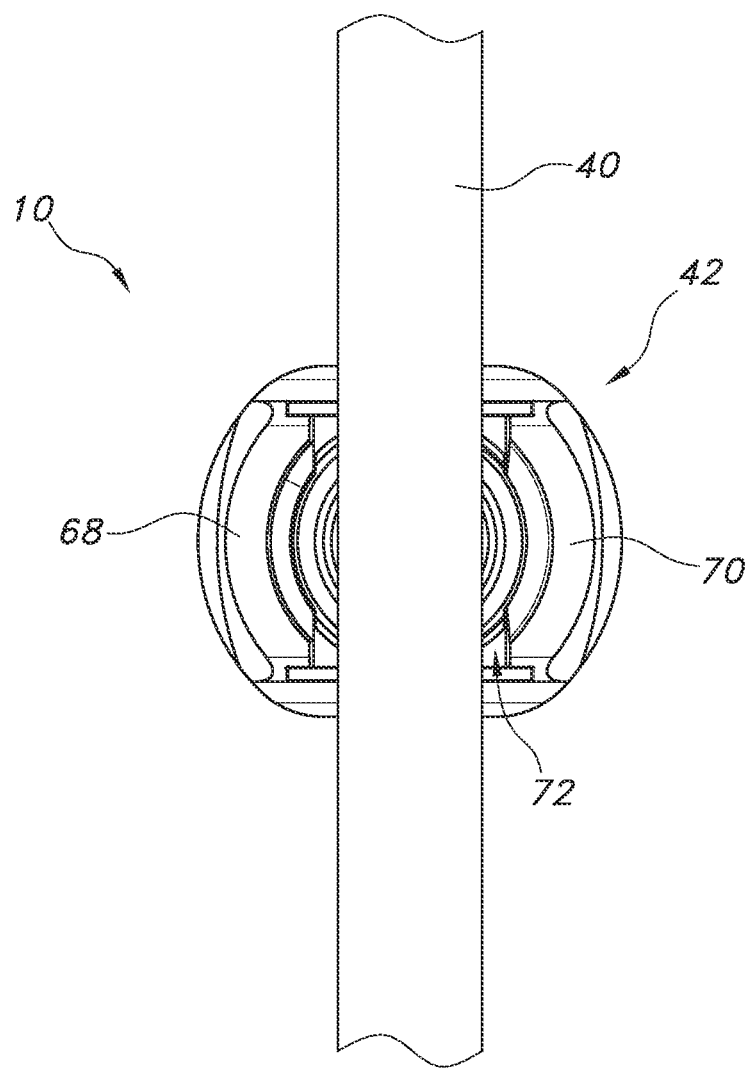
FIG. 6 is a plan view showing the bone fastener shown in FIG. 4 disposed with vertebra and the spinal rod shown in FIG. 5 disposed with the bone fastener.
Figure 7:
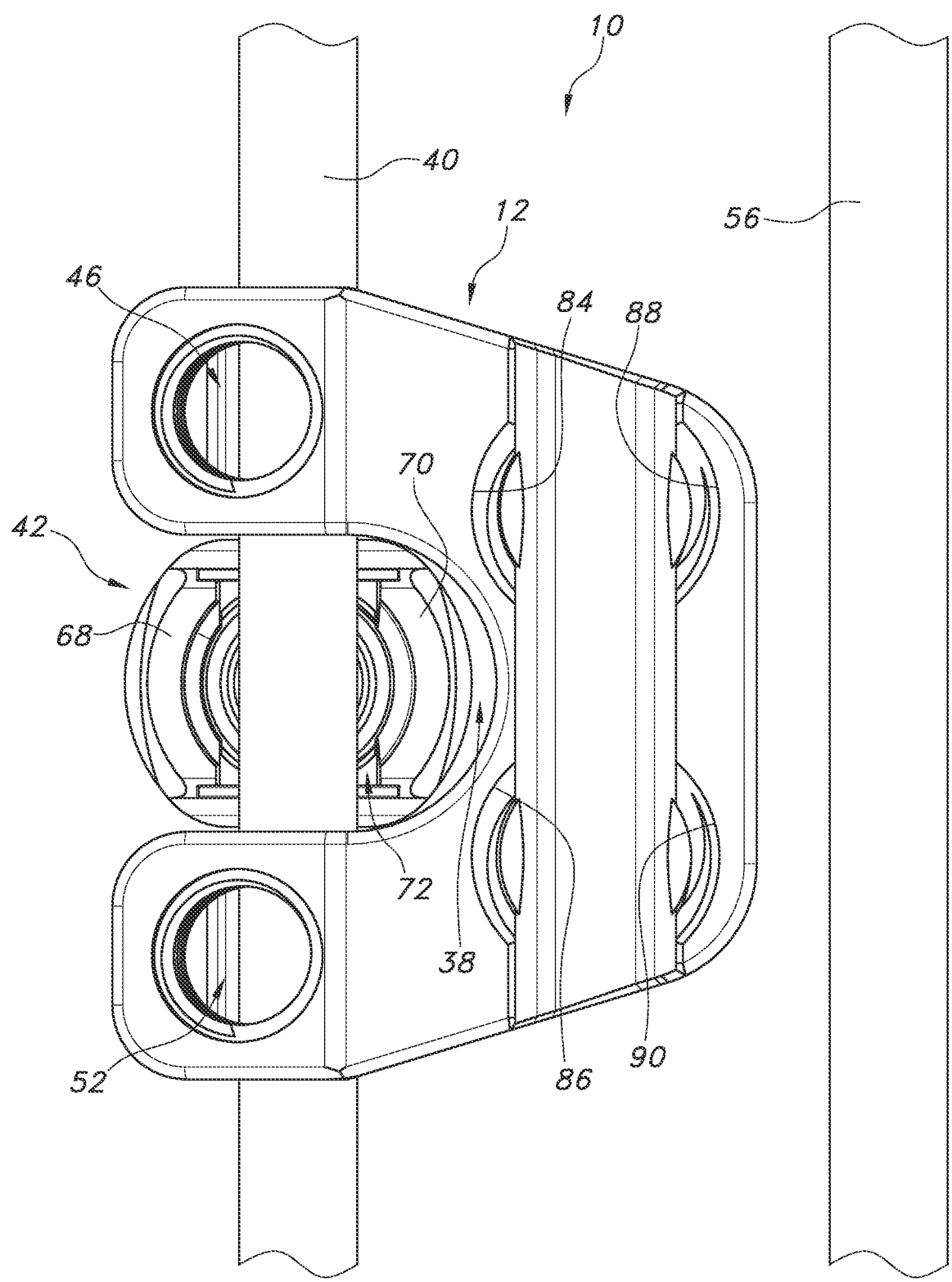
FIG. 7 is a plan view showing the spinal implant shown in FIG. 1 disposed with the spinal rod shown in FIG. 5 and a revision rod of the surgical system, in accordance with the principles of the present disclosure.
Figure 8:
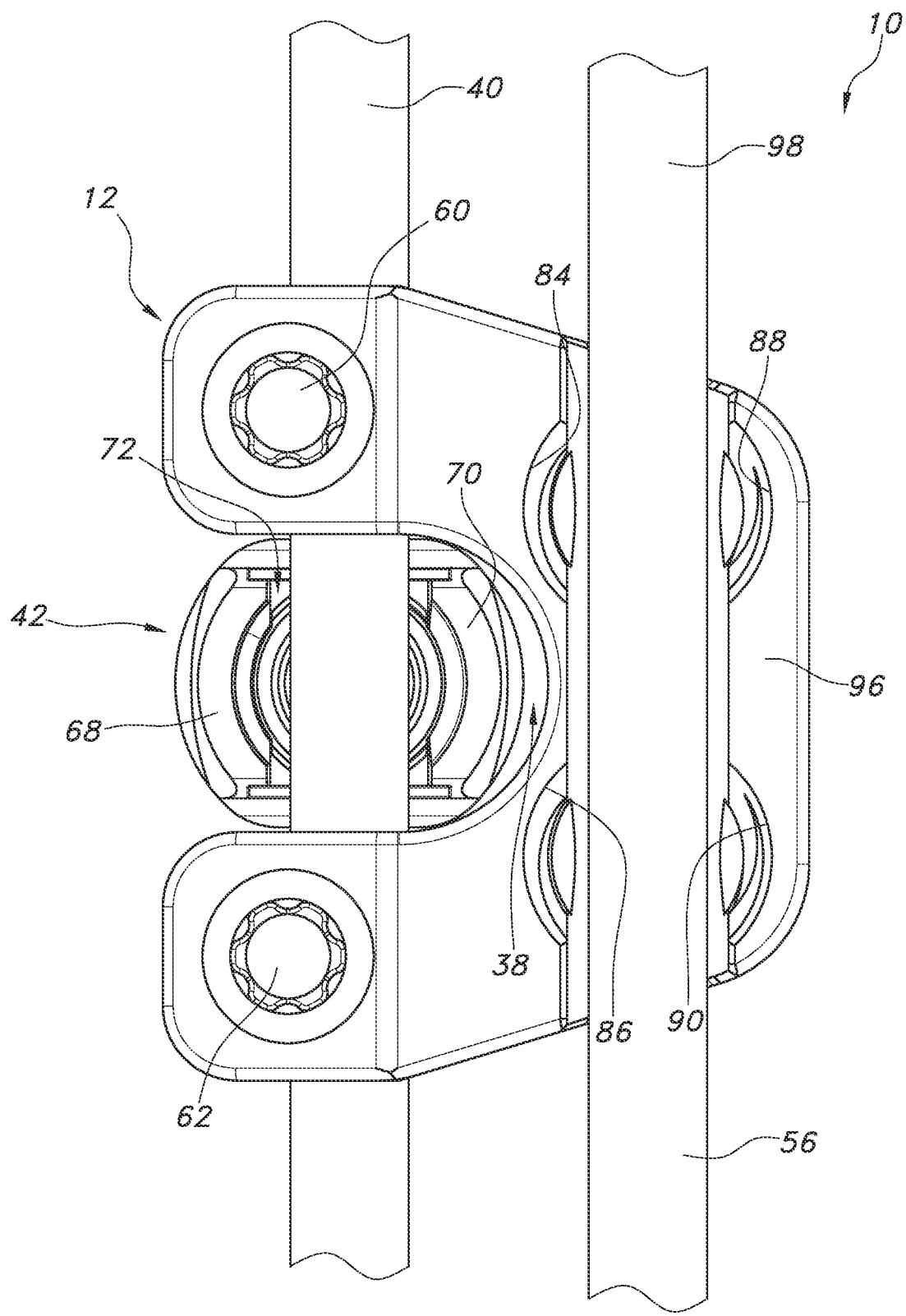
FIG. 8 is a plan view showing the spinal implant shown in FIG. 1 disposed with the spinal rod shown in FIG. 5 and the revision rod shown in FIG. 7.
Figure 9:
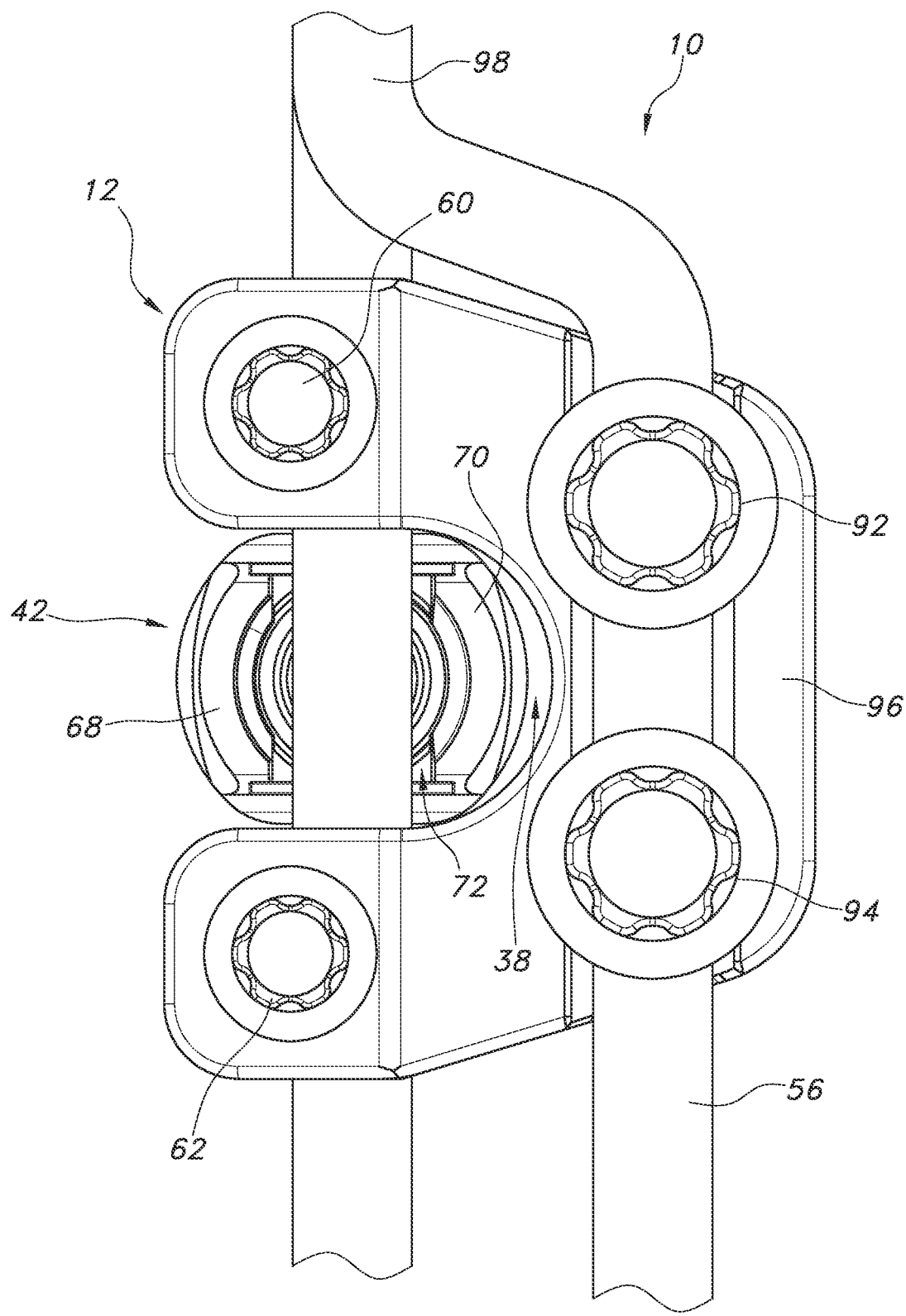
FIG. 9 is a plan view showing the spinal implant shown in FIG. 1 disposed with the spinal rod shown in FIG. 5 and the revision rod shown in FIG. 7, wherein the revision rod is bent to be parallel or substantially with the spinal rod.

A surgical system, such as, for example, a spinal implant system 10 includes a domino, such as, for example, a spinal implant 12, as best shown in FIGS. 1-3. Implant 12 includes a body 14 having a wall 16. Implant 12 includes a portion 18 comprising spaced apart assemblies 20, 22 each extending from a side 24 of wall 16. Assembly 20 comprises spaced apart extensions 26, 28 and assembly 22 comprises spaced apart extensions 30, 32. Extensions 26, 28 define a bay or opening 34 and extensions 30, 32 define a bay or opening 36. Openings, 34, 36 extend parallel to one another and/or are coaxial and configured for disposal of an existing spinal rod, such as, for example, rod 40, as shown in FIGS. 7-9. That is, rod 40 is configured to be inserted into openings 34, 36 after rod 40 is coupled to tissue, such as, for example, vertebral tissue by a fastener, such as, for example, a bone fastener 42, as shown in FIGS. 5 and 6, and discussed in greater detail herein. In some embodiments, implant 12 is monolithic and/or integrally formed.

In some embodiments, extension 26 includes a surface 44 defining a threaded hole 46 extending therethrough and a surface 48 extending from surface 44. In some embodiments, extension 30 includes a surface 50 defining a threaded hole 52 extending therethrough and a surface 54 extending from surface 50. Hole 46 is configured for disposal of a set screw 60 and hole 52 is configured for disposal of a set screw 62, as shown in FIGS. 8 and 9, such that set screws 60, 62 directly engage rod 40 when rod 40 is disposed in openings 34, 36 to fix rod 40 relative to implant 12, as discussed herein.

In some embodiments, surface 48 extends at an acute angle relative to surface 44 and surface 54 extends at an acute angle relative to surface 50. Angling surfaces 48, 54 relative to surfaces 44, 50 provides space for disposal of a rod bender to bend a spinal rod, such as, for example, a revision rod 56 that is disposed in a channel 58 of implant 12 so that at least a portion of rod 56 can be bent to be parallel or substantially parallel with rod 40, as shown in FIG. 9 and discussed in greater detail herein. Hole 46 extends transverse and/or perpendicular to opening 34 and hole 52 extends transverse and/or perpendicular to opening 36 such that holes 46, 52 extend parallel to one another, hole 46 is in communication with opening 34 and hole 52 is in communication with opening 36. In some embodiments, surfaces 44, 50 extend parallel to one another and lie in a common plane. In some embodiments, surfaces 48, 54 extend parallel to one another and lie in a common plane.

Figure 4:
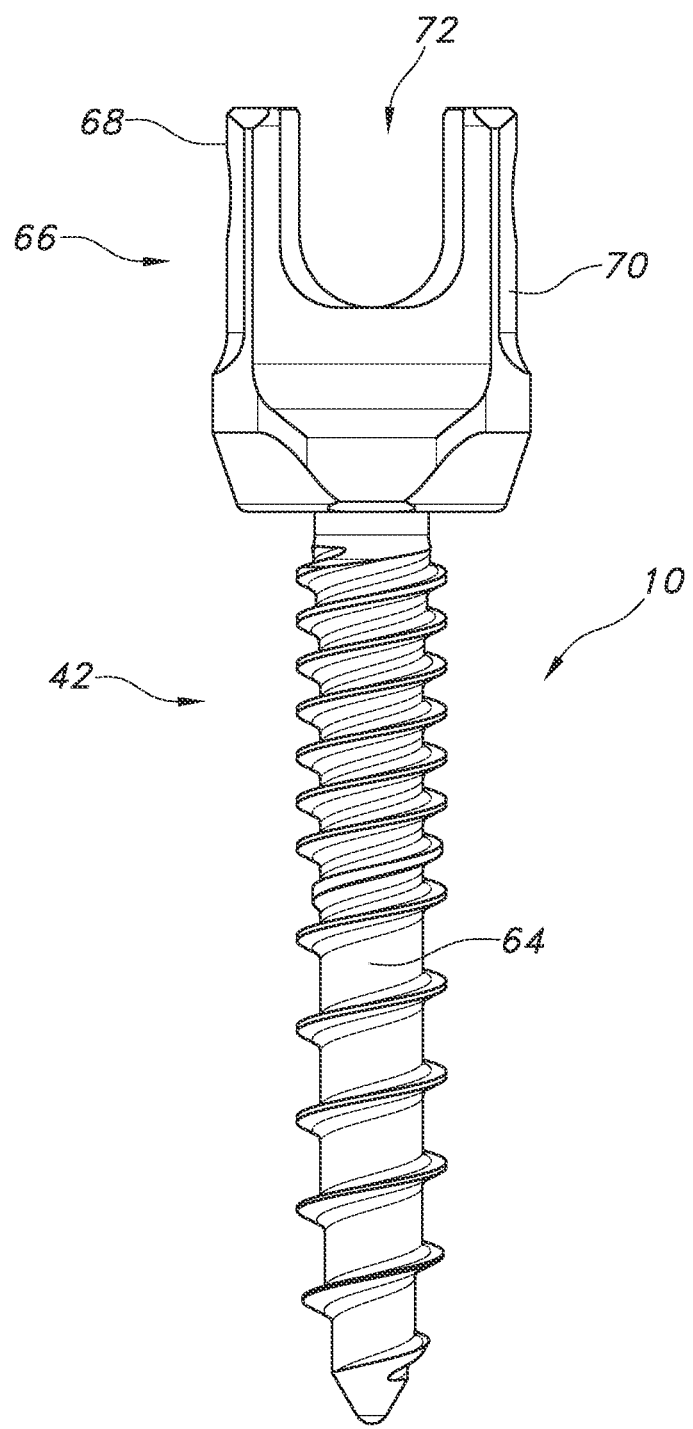
FIG. 4 is a side view of a bone fastener of the surgical system, in accordance with the principles of the present disclosure.

A space between assemblies 20, 22 defines a cavity 38 configured for disposal of at least a portion of bone fastener 42. In particular, bone fastener 42 includes a shaft 64 and a head 66 coupled to shaft 64, as best shown in FIG. 4. Head 66 is configured for disposal in cavity 38 and includes spaced apart arms 68, 70 that define an implant cavity 72 therebetween configured for disposal of rod 40, as shown in FIGS. 6-9. In particular, in some embodiments, implant cavity 72 is aligned and/or coaxial with openings 34, 36 such that rod 40 can be inserted into openings 34, 36 when rod 40 is disposed in implant cavity 72 and head 66 is positioned in cavity 38, as discussed herein. In some embodiments, head 66 is integrally formed with shaft 64 such that head 66 is permanently fixed relative to shaft 64. In some embodiments, head 66 is rotatable relative shaft 64 in a plurality of planes and/or axes to define a polyaxial screw.

Implant 12 includes a portion 74 extending from a side 76 of wall 16 that is opposite side 24. Portion 74 comprises a wall 78 that is spaced apart from wall 16. Opposing surfaces 80, 82 of walls 16, 78 define channel 58. In some embodiments, channel 58 extends parallel to openings 34, 36. Surface 80 includes spaced apart threads 84, 86 and surface 82 includes spaced apart threads 88, 90. Threads 84, 86 are configured for engagement with a set screw 92 and threads 88, 90 are configured for engagement with a set screw 94, as shown in FIG. 9, such that set screws 92, 94 directly engage rod 56 when rod 56 is positioned in channel 58 to fix rod 56 relative to implant 12, as discussed herein.

In operation and use, system 10 may be used to revise an existing rod, such as, for example, rod 40 that is implanted in a patient to lengthen rod 40, for example. In particular, shaft 64 may be threaded with tissue, such as, for example, vertebral tissue and rod 40 is inserted into implant cavity 72, as shown in FIGS. 5 and 6. In some embodiments, inner surfaces of arms 68, 70 are threaded for engagement with a set screw and the set screw is threaded with the inner surfaces of arms 68, 70 such that the set screw directly engages rod 40 to fix rod 40 relative to head 66.

Once rod 40 and bone fastener 42 are disposed with the vertebral tissue, implant 12 is connected with rod 40 and bone fastener 42 by inserting head 66 into cavity 38 such that implant cavity 72 is aligned with openings 34, 36 to position rod 40 simultaneously in implant cavity 72 and openings 34, 36, as shown in FIG. 7. At this point, set screws 60, 62 may be threaded with holes 46, 52, as shown in FIG. 8, such that set screws 60, 62 directly engage rod 40 to fix rod 40 relative to implant 12. Rod 56 may be placed into channel 58, as shown in FIG. 8, either before or after screws 60, 62 are threaded with holes 46, 52 such that set screws 60, 62 directly engage rod 40 to fix rod 40 relative to implant 12. In particular, a section 96 of rod 56 is positioned in channel 58, while a section 98 of rod 56 is disposed outside of channel 58. Section 98 is then bent, using a rod bender for example, such that section 98 extends parallel or substantially parallel to rod 40, thus effectively lengthening rod 40 using rod 56, as shown in FIG. 9. In some embodiments, opposing surfaces 16a, 16b of wall provide space for disposal of the rod bender to bend rod 56 when rod 56 is disposed in channel 58 so that section 98 can be bent to be parallel or substantially parallel with rod 40, as shown in FIG. 9. That is, surfaces 16a, 16b provide clearance to connect the rod bender with rod 56 and manipulate rod 56 to bend rod, as discussed herein. In some embodiments, surfaces 16a, 16b provide 585 space for a bent rod. For example, in some embodiments, angling surfaces 48, 54 relative to surfaces 44, 50 provides space for a portion of a spinal rod that extends at a non-zero angle relative to another portion of the spinal rod.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A spinal implant comprising:
   a body including a first wall, the first wall comprising opposite proximal and distal surfaces;
   a first portion comprising spaced apart first and second assemblies each extending from a first side of the first wall, the first assembly comprising spaced apart first and second extensions, the second assembly comprising spaced apart third and fourth extensions, the first and second extensions defining a first opening, the third and fourth extensions defining a second opening, the first and third extensions each including a proximal surface extending from the proximal surface of the first wall, the proximal surface of the first wall extending at an acute angle relative to a longitudinal axis defined by the first wall, the proximal surfaces of the first and third extensions each extending at an acute angle relative to the proximal surface of the first wall, the proximal surface of the first extension defining a first threaded hole, the proximal surface of the third extension defining a second threaded hole, a space between the first assembly and the second assembly defining a cavity configured for disposal of a head of a bone fastener, the cavity extending through the proximal and distal surfaces, the head and the openings being configured for disposal of a first spinal rod therein; and
   a second portion extending from an opposite second side of the first wall, the second portion comprising a second wall that is spaced apart from the first wall, opposing surfaces of the walls defining a channel configured for disposal of a second spinal rod, the channel extending through the proximal surface along an entire length of the channel.

2. The spinal implant recited in claim 1, wherein the openings extend parallel to the channel.

3. The spinal implant recited in claim 1, wherein the first threaded hole extends at an acute angle relative to the proximal surface of the first extension and the second threaded hole extends at an acute angle relative to the proximal surface of the third extension.

4. The spinal implant recited in claim 1, wherein the holes extend parallel to one another.

5. The spinal implant recited in claim 1, wherein the holes extend transverse to the openings.

6. The spinal implant recited in claim 1, wherein the first hole is in communication with the first opening and the second hole is in communication with the second opening.

7. The spinal implant recited in claim 1, wherein the first wall extends along a longitudinal axis from the proximal surface of the first wall to the distal surface of the first wall, the proximal surfaces each extending at an acute angle relative to the longitudinal axis.

8. The spinal implant recited in claim 1, wherein the second side includes spaced apart first and second threads.

9. The spinal implant recited in claim 8, wherein the second wall includes spaced apart third and fourth threads, the first and third threads being configured for disposal of a first set screw, the second and fourth threads being configured for disposal of a second set screw.

10. The spinal implant recited in claim 1, wherein the spinal implant is monolithic.

11. A surgical system comprising:
    a spinal implant including a body having a first wall, the first wall comprising opposite proximal and distal surfaces, the spinal implant including a first portion comprising spaced apart first and second assemblies each extending from a first side of the first wall, the first assembly comprising spaced apart first and second extensions, the second assembly comprising spaced apart third and fourth extensions, the first and second extensions defining a first opening, the third and fourth extensions defining a second opening, the first and third extensions each including a proximal surface extending from the proximal surface of the first wall, the proximal surface of the first wall extending at an acute angle relative to a longitudinal axis defined by the first wall, the proximal surfaces of the first and third extensions each extending at an acute angle relative to the proximal surface of the first wall, the proximal surface of the first extension defining a first threaded hole, the proximal surface of the third extension defining a second threaded hole, a space between the first assembly and the second assembly defining a cavity, the cavity extending through the proximal and distal surfaces, the spinal implant including a second portion extending from an opposite second side of the first wall, the second portion comprising a second wall that is spaced apart from the first wall, opposing surfaces of the walls defining a channel, the channel extending through the proximal surface along an entire length of the channel;
a bone fastener having a head positioned in the cavity;
a first spinal rod disposed in the head and the openings; and
a second spinal rod disposed in the channel.

12. The surgical system recited in claim 11, further comprising a first set screw disposed in the first threaded hole and a second set screw disposed in the second threaded hole such that the set screws directly engage the first spinal rod.

13. The surgical system recited in claim 11, wherein the first wall extends along a longitudinal axis from the proximal surface of the first wall to the distal surface of the first wall, the proximal surfaces each extending at an acute angle relative to the longitudinal axis.

14. The surgical system recited in claim 13, further comprising a first set screw disposed in the first threaded hole and a second set screw disposed in the second threaded hole such that the set screws directly engage the first spinal rod.

15. The surgical system recited in claim 11, wherein the second side includes spaced apart first and second threads.

16. The surgical system recited in claim 15, wherein the second wall includes spaced apart third and fourth threads, the surgical system comprising a first set screw disposed with the first and third threads and a second set screw disposed with the second and fourth threads such that the set screws directly engage the second spinal rod.

17. The surgical system recited in claim 11, wherein the first hole is in communication with the first opening and the second hole is in communication with the second opening.

18. The surgical system recited in claim 17, wherein the holes extend parallel to one another, the first threaded hole extending at an acute angle relative to the proximal surface of the first extension and the second threaded hole extending at an acute angle relative to the proximal surface of the third extension.

19. The surgical system recited in claim 17, wherein the holes extend transverse to the openings.

20. A surgical system comprising:
a monolithic spinal implant including a body having a first wall, the first wall extending along a longitudinal axis between opposite proximal and distal surfaces, the spinal implant including a first portion comprising spaced apart first and second assemblies each extending from a first side of the first wall, the first assembly comprising spaced apart first and second extensions, the second assembly comprising spaced apart third and fourth extensions, the first and second extensions defining a first opening, the third and fourth extensions defining a second opening, the first and third extensions each including a proximal surface extending from the proximal surface of the first wall, the proximal surface of the first wall extending at an acute angle relative to a longitudinal axis defined by the first wall, the proximal surfaces of the first and third extensions each extending at an acute angle relative to the proximal surface of the first wall, the proximal surface of the first extension defining a first threaded hole that extends at an acute angle relative to the proximal surface of the first extension, the proximal surface of the third extension defining a second threaded hole that extends parallel to the first hole, the second hole extending at an acute angle relative to the proximal surface of the third extension, a space between the first assembly and the second assembly defining a cavity, the cavity extending through the proximal and distal surfaces, a concave portion of the cavity extending into the first wall, proximal surfaces of the first and third extensions each being flush with the proximal surface of the first wall, distal surfaces of the second and fourth extensions each being flush with the distal surface of the first wall, the spinal implant including a second portion extending from an opposite second side of the first wall, the second portion comprising a second wall that is spaced apart from the first wall, opposing surfaces of the walls defining a channel, the channel extending through the proximal surface along an entire length of the channel;
a bone fastener having a head positioned in the cavity;
a first spinal rod disposed in the head and the openings; and
a second spinal rod disposed in the channel,
wherein the proximal surfaces each extend transverse to the longitudinal axis,
wherein the surgical system further comprises a first set screw disposed in the first threaded hole and a second set screw disposed in the second threaded hole such that the set screws directly engage the first spinal rod,
wherein the second side includes spaced apart first and second threads, and
wherein the second wall includes spaced apart third and fourth threads, the surgical system comprising a third set screw disposed with the first and third threads and a fourth set screw disposed with the second and fourth threads such that the third and fourth set screws directly engage the second spinal rod.

* * * * *